United States Patent [19]
Uchio et al.

[11] 4,040,906
[45] Aug. 9, 1977

[54] METHOD OF PRODUCING CARBON SOURCE FOR CITRIC ACID FERMENTATION

[75] Inventors: Ryosuke Uchio, Zushi; Kenji Kikuchi, Yokosuka; Soichiro Asai, Tokyo; Kenichi Yarita, Yokohama, all of Japan

[73] Assignee: Ajinomoto Co., Inc., Tokyo, Japan

[21] Appl. No.: 679,711

[22] Filed: Apr. 23, 1976

[51] Int. Cl.$^2$ .................... C12D 1/04; C12B 3/04
[52] U.S. Cl. ................... 195/36 R; 195/102
[58] Field of Search .......... 195/36 R, 37, 35, 100, 195/102, 31 F, 106; 127/41

[56] References Cited

U.S. PATENT DOCUMENTS

| 2,492,673 | 12/1949 | Woodward et al. | 195/36 R |
| 3,793,146 | 2/1974 | Ishii et al. | 195/37 |
| 3,812,010 | 5/1974 | Nitsch | 195/31 F |

*Primary Examiner*—Lionel M. Shapiro
*Attorney, Agent, or Firm*—Oblon, Fisher, Spivak, McClelland & Maier

[57] ABSTRACT

A sugar hydrolyzate, containing both glucose and fructose, is mixed with calcium hydroxide, and a fructose addition precipitate is recovered. The residual liquor is neutralized, calcium ions are removed, and then the liquor is used as a carbon source for citric acid fermentation.

The present method may supply very inexpensive fructose to the market.

5 Claims, No Drawings

METHOD OF PRODUCING CARBON SOURCE FOR CITRIC ACID FERMENTATION

BACKGROUND OF THE INVENTION

1. Field of the Invention

This invention relates to a method of producing a novel carbon source for fermentation, and also to provide a very inexpensive source of fructose which is economically comparable to sucrose.

2. Description of the Prior Art

Fructose has a comfortable sweetness, and it is about 1.5 - 2 times as sweet as sucrose. There have been known many manufacturing processes for fructose, however, the manufacturing cost is too expensive and accordingly its market is restricted to such special uses as for foods for diabetics.

Sucrose is widely employed as a raw material for the production of fructose. However, it is difficult to treat the mother liquor after the fructose has been recovered. Many methods of treating the mother liquor have been investigated, for example, treating with glucose isomerase, but so far no economically satisfactory process has been developed.

It has been reported in U.S. Pat. No. 3,793,146 that fructose is recovered from a sucrose hydrolyzate in the form of an addition product with calcium chloride and the mother liquor is used as a main carbon source for fermentation of citric acid. However, the fructose produced by the method described in that U.S. patent is expensive because in the calcium chloride method, the sucrose must be pure. Furthermore, the kind of fermentation is limited because a large quantity of calcium ions and chloride ions remain in the mother liquor and inhibit the fermentation.

SUMMARY OF THE INVENTION

It has now been found that when fructose is recovered from a sucrose hydrolyzate in the form of an addition product of calcium hydroxide, and when the mother liquor, wherein the calcium ions are eliminated, is neutralized, the mother liquor is suitable as a carbon source of a fermentation of citric acid by using a strain belonging to species *Aspergillus niger* or *A. awamori*.

DETAILED DESCRIPTION OF THE PREFERRED EMBODIMENTS

Raw material applicable to the present invention include various products and intermediates produced in the sugar manufacturing process from cane and beet, such as juices of cane and beet, crude sugar, and molasses.

Hydrolysis of sucrose in the raw material may be carried out by known methods, such as by the use of mineral acid or an enzyme. For example, if the pH of the raw material is adjusted to 1.5 - 2 with hydrochloric acid and is heated to 60° - 100° C for 0.5 - 4 hours, most of the sucrose may be hydrolyzed to hexose, i.e., glucose and fructose.

When the raw material is hydrolyzed with mineral acid, the hydrolyzate is neutralized with an alkali, such as calcium hydroxide, preferably in an amount of 0.7 - 1.5 times the molar quantity of the hexose. Instead of calcium hydroxide, calcium oxide may be employed. In this instance, calcium oxide is first converted to calcium hydroxide in the hydrolyzate, and then reacted with fructose.

The mixing must be carried out cautiously. First, the neutral hydrolyzate is cooled to below 10° C, preferably below 5° C, and calcium hydroxide, in an amount of 1.2 - 1.6 times the molar quantity of the fructose, is added to the cold hydrolyzate. Then, the seed adducts of fructose and calcium hydroxide are preferably added, and the seeded mixture is aged for 15 - 60 minutes with moderate stirring. The adduct crystals may also crystallize without seeding. The remaining calcium hydroxide, is added gradually over a period of about 1 - 2 hours. During the reaction of calcium hydroxide with fructose, the temperature of the reactant is preferably kept below 5° C in order to decrease the decomposition of fructose and glucose. The above procedure produces large crystals of the adduct which are especially suitable for separation on an industrial scale.

Unless the mixing is carried out with caution, the resulting slurry will be creamy and will consist of mainly fine crystals. Accordingly, separation of crystals on an industrial scale will be difficult.

If the neutral hydrolyzate is mixed with calcium chloride instead of calcium hydroxide, the adduct crystals cannot be separated because the crystals precipitated will be fine and the slurry will be highly viscous.

The crystals so produced are recovered by filtering or centrifuging. The recovered crystals are preferably washed with chilled water.

Fructose crystals or a fructose solution containing small amount of glucose, can be prepared from the recovered crystals by known methods. The most preferable neutralizing agent for calcium hydroxide in the adduct is carbon dioxide. In this case, the crystals are placed into water, and then carbon dioxide gas is bubbled into the suspension. After the bubbling, the precipitate is removed thereby providing the crude fructose solution. The fructose solution can, if desired, further be purified by known methods, such as crystallization, ion exchange resin methods, and decolorization to prepare the final fructose crystals.

The yield of fructose from the hydrolyzate in the above solution may be as high as 70%, usually 50 - 65%.

The mother liquor is neutralized, and calcium ions are removed from the liquor. Suitable neutralizing agents include carbon dioxide, sulfuric acid, phosphoric acid, cation exchange resins, or the like. When the neutralization is carried out by use of one of said exemplified agents, calcium ions can be removed simultaneously. Among the above agents, carbon dioxide is the most preferable, because recovered calcium carbonate can be used again by calcination. The other superiority of carbon dioxide is decolorization effect during neutralization.

Since both fructose and glucose are not stable in alkali solution, it is necessary that fructose and glucose are kept cold throughout the above procedure. It is also necessary that after fructose adduct is separated, both the adduct and the mother liquid is quickly neutralized.

The calcium-eliminated mother liquid is suitable for carbon source for citric acid fermentation by using a strain belonging to species *Aspergillus niger* or *A. awamori*. Examples of the strain are:

| Aspergillus niger | ATCC 6275 |
|---|---|
| A. awamori | FERM-P 3512 |

Microorganisms identified by FERM-P numbers are available to the public from the Fermentation Research Institute, Agency of Industrial Science and Technology of the Ministry for International Trade and Industry, Japan.

Fermentation is carried out according to the conventional manner.

The yield of citric acid from the mother liquid of the present invention is much higher than the same from the raw material which is the conventional carbon source for citric acid fermentation. Particularly in case of molasses, in spite of lowering carbon purity by extracting fructose, the yield of the present method is also much higher than the yield of the conventional method.

EXAMPLE 1

A solution containing 1 kg crude sugar per one liter of water was prepared, adjusted to pH 1.5 with sulfuric acid, and hydrolyzed at 60° C for 4 hours. The hydrolyzate was neutralized with calcium hydroxide, and precipitates of calcium sulfate were filtered out.

3 kg Invert sugar solution containing 303 g fructose and 297 g glucose was cooled to 0° C and 30% calcium hydroxide containing 260 g Ca(OH)$_2$ was gradually added to the solution so that the temperature was kept below 5° C. When 60% amount of total calcium hydroxide was added, the addition was stopped and a small amount of the adduct crystals were seeded. The remaining 40% amount of calcium hydroxide was then gradually added, and the slurry so produced was aged for 30 minutes. The adduct crystals were filtered off, and washed sufficiently with chilled water.

The recovered crystals were suspended into chilled water, and the suspension was neutralized until below pH 10 by introducing carbon dioxide gas at 0° C. The precipitates of calcium carbonate were filtered, and the filtrate of which pH was about 8.5 was concentrated to 420 g. The concentrated solution contained 202 g fructose (Yield; 66.7%) and 8 g glucose. The concentrated solution was passes through two columns, one was packed with strongly acidic cation exchange resin and the other was packed with weakly basic anion exchange resin, and accordingly the solution was desalted and partially decolorized. The effluent was further treated with activated carbon, concentrated, and colorless solution (fructose concentration; 70%) was obtained.

The mother liquor was also neutralized until below pH 10 by introducing carbon dioxide gas at 0° C, and the precipitate was removed. The pH of the filtrate was about 8.5. The filtrate was concentrated, and 896 g of the concentrated calcium-eliminated mother liquor containing 85 g fructose and 274 g glucose was obtained.

Four batches of the fermentation test were carried out using the starting material of crude sugar and the concentrated calcium-eliminated mother liquor as a main carbon source.

Each 20 ml culture medium containing:

| One of the above main carbon sources | 15 g/dl (as hexose) |
|---|---|
| NH$_4$NO$_3$ | 0.25 g/dl |
| KH$_2$PO$_4$ | 0.01 " |
| MgSO$_4$ . 7H$_2$O | 0.25 " |
| MnSO$_4$ . 4H$_2$O | 0.0005 " |
| ZnSO$_4$ . 7H$_2$O | 0.0001 " |
| CuSO$_4$ . 5H$_2$O | 0.00002" | was prepared, placed in 500 ml shaking flask, and sterilized.

Each medium was inoculated with *Aspergillus niger* ATCC 6275 or *A. awamori* FERM-P 3512, and cultured at 30° C for 7 days with shaking. After the culturing, the citric acid concentration of the broth was determined and shown in Table 1.

TABLE 1

| | Citric acid | |
|---|---|---|
| Carbon source | A. niger ATCC 6275 | A. awamori FERM-P 3512 |
| Crude sugar | 4.55 g/dl | 3.35 g/dl |
| Ca-eliminated mother liquor | 6.25 | 4.26 |

EXAMPLE 2

Cane molasses was diluted with 2.3 l water per kg cane molasses, adjusted to pH 1.5 with sulfuric acid, and hydrolyzed at 60° C for 4 hours. The hydrolyzate was neutralized with calcium hydroxide, and precipitates of calcium sulfate were filtered out. Accordingly, invert sugar solution containing 9.95 g/dl glucose and 11.25 g/dl fructose was prepared.

Three liters of the invert sugar solution was cooled to 0° C and 30% calcium hydroxide containing 262 g Ca(OH)$_2$ (equal mole to hexose) was gradually added to the solution so that the temperature was kept below 5° C. When 70% amount of total calcium hydroxide was added, the addition was stopped and a small amount of the adduct crystals were seeded. For decreasing the supersaturation, the seeded solution was stirred for 30 minutes. During stirring, many adduct crystals crystallized out. The remaining 30% amount of calcium hydroxide was then gradually added for one hour, and the slurry so produced was further stirred for 30 minutes. The adduct crystals were filtered off, and washed with chilled water.

The recovered crystals were suspended into chilled water, the suspension was neutralized with sulfuric acid, and the precipitate formed was removed. The fructose solution so produced contained 168 g fructose and 6.4 g glucose. The yield of fructose was 50%.

The mother liquor was also neutralized with sulfuric acid, and the precipitate was removed. The calcium-eliminated mother liquor contained 284 g glucose and 159 g fructose.

The citric acid fermentation tests were carried out in the same manner as described in Example 1, except that the crude sugar and its concentrated calcium-eliminated mother liquor were replaced by the cane molasses and its concentrated calcium-eliminated mother liquor.

The fermentation results are shown in Table 2.

TABLE 2

| | Citric acid | |
|---|---|---|
| Carbon source | A. niger ATCC 6275 | A. awamori FERM-P 3512 |
| Cane molasses | 4.42 g/dl | 2.82 g/dl |
| Ca-eliminated mother liquor | 5.81 | 3.84 |

EXAMPLE 3

Beet molasses was diluted with 2.5 l water per kg beet molasses, adjusted to pH 1.5 with sulfuric acid, and hydrolyzed at 60° C for 4 hours. The hydrolyzate was neutralized with calcium hydroxide, the precipitates formed were filtered out. Accordingly, invert sugar solution containing 7.80 g/dl glucose and 8.81 g/dl fructose was prepared.

Three liters of the invert sugar solution was cooled to 0° C and 30% calcium hydroxide containing 205 g Ca(OH)$_2$ (equal mole to hexose) was gradually added to the solution so that the temperature was kept below 5° C. When 70% the amount of total calcium hydroxide was added, the addition was stopped and a small amount of the adduct crystals were seeded. For decreasing the supersaturation, the seeded solution was stirred for 30 minutes. During stirring, many adduct crystals crystallized out. The remaining 30% amount of calcium hydroxide was then gradually added for one hour, and the slurry so produced was further stirred for 30 minutes. The adduct crystals were filtered off, and washed with chilled water.

The recovered crystals were suspended into chilled water, the suspension was neutralized with sulfuric acid, and the precipitate formed was removed. The fructose solution so produced contained 169 g fructose (Yield: 64%) and 6.3 g glucose.

As to the mother liquor, it was also neutralized with sulfuric acid, and the precipitate was removed. The calcium-eliminated mother liquor contained 220 g glucose and 87 g fructose.

The citric acid fermentation tests were carried out in the same manner as described in Example 1, except that the crude sugar and its concentrated calcium-eliminated mother liquor were replaced by the beet molasses and its concentrated calcium-eliminated mother liquor.

The fermentation results are shown in Table 3.

TABLE 3

| Carbon source | Citric acid | |
| --- | --- | --- |
| | A. niger ATCC 6275 | A. awamori FERM-P 3512 |
| Beet molasses | 3.48 g/dl | 1.64 g/dl |
| Ca-eliminated mother liquor | 4.52 | 2.85 |

What is claimed as new and intended to be covered by Letters Patent is:

1. In the fermentation production of citric acid wherein fermentation is effected by the use of a microorganism of the species *Aspergillus niger* or *Aspergillus awamori*, the improvement which comprises:
    admixing a substantially neutral hydrolyzate of juices of cane or beet, crude sugar, or molasses containing glucose and fructose cooled to below 10° C with calcium hydroxide to form a fructose addition product precipitate, and
    neutralizing the remaining mother liquor, simultaneously eliminating calcium ions therefrom, and utilizing the remaining liquor as the carbon source for said fermentation.
2. The method of claim 1 wherein the pH of the molasses is adjusted to 1.5 – 2 and thereafter hydrolyzed at a temperature of 60° – 100° C for 0.5 to 4 hours.
3. The method of claim 2, wherein the hydrolyzed molasses is neutralized with an alkali and thereafter calcium hydroxide is added thereto to precipitate the fructose addition product.
4. The method of claim 3, wherein neutralizing the mother liquor and simultaneously eliminating calcium ions is accomplished by introducing carbon dioxide gas and precipitation of calcium carbonate.
5. The method of claim 3, wherein neutralizing the mother liquor and simultaneously eliminating calcium ions is accomplished by the addition of sulfuric acid.

* * * * *